United States Patent [19]

Hiratani et al.

[11] Patent Number: 5,599,935
[45] Date of Patent: Feb. 4, 1997

[54] BISQUINOLINOL AND BISBENZOQUINOLINOL COMPOUNDS, AND PROCESS FOR PRODUCING SAME

[75] Inventors: Kazuhisa Hiratani; Toshikazu Takahashi, both of Tsukuba; Kazuyuki Kasuga, Tsuchiura; Hideki Sugihara, Tsukuba, all of Japan

[73] Assignee: Director-General of Industrial Science and Technology, Japan

[21] Appl. No.: 552,860

[22] Filed: Nov. 3, 1995

[30] Foreign Application Priority Data

Nov. 17, 1994 [JP] Japan .................................. 6-283083

[51] Int. Cl.$^6$ .................................................. C07D 401/06
[52] U.S. Cl. ............................................ 546/101; 546/178
[58] Field of Search ..................................... 546/178, 101

[56] References Cited

PUBLICATIONS

Analytical Sciences, Jun. 1993, vol. 9, pp. 355–359.

*Primary Examiner*—David B. Springer
*Attorney, Agent, or Firm*—Lorusso & Loud

[57] ABSTRACT

A bisquinolinol or bisbenzoquinolinol compound is disclosed which has the formula $CH_2=C(CH-R^1)_2$ wherein $R^1$ represents a 8-hydroxy-7-quinolyl group which may have an alkyl group at the 2-position thereof or a 10-hydroxy-9-benzoquinolyl group which may have an alkyl group at the 2-position thereof. The bisquinolinol and bisbenzoquinolinol compounds may be obtained by thermal rearrangement of a bisquinoline or bisbenzoquinoline compound of the formula $CH_2=C(CH_2-O-R^2)_2$ wherein $R^2$ represents a 8-quinolyl group which may have an alkyl group at the 2-position thereof or a 10-benzoquinolyl group which may have an alkyl group at the 2-position thereof. The bisquinolinol and bisbenzoquinolinol compounds are useful as an extractant for metal ions.

4 Claims, No Drawings

BISQUINOLINOL AND BISBENZOQUINOLINOL COMPOUNDS, AND PROCESS FOR PRODUCING SAME

BACKGROUND OF THE INVENTION

This invention relates to a novel bisquinolinol or bisbenzoquinolinol compound, to an intermediate compound thereof, to a process for the production thereof and to a use thereof for extracting metal ions.

It is known to use 8-quinolinol or 10-benzoquinolinol as an extractant for metal ions. The known extractants, however, are disadvantageous, because the metal-capturing power is not fully satisfactory. Additionally, the known extractants have problems because they fail to show preference to specific metal ions or because their extraction performance depends upon the pH of the liquid from which metal ions are extracted.

SUMMARY OF THE INVENTION

It is, therefore, the prime object of the present invention to provide novel bisquinolinol and bisbenzoquinolinol compounds which have high metal-capturing power.

Another object of the present invention is to provide novel bisquinolinol and bisbenzoquinolinol compounds which can selectively capture specific metal ions.

It is a further object of the present invention to provide novel bisquinolinol and bisbenzoquinolinol compounds which can capture metal ions contained in a liquid with a wide pH range.

It is a further object of the present invention to provide novel compounds which can be easily converted into the above novel bisquinolinol and bisbenzoquinolinol compounds.

It is yet a further object of the present invention to provide a process for the production of the above novel bisquinolinol and bisbenzoquinolinol compounds.

It is yet a further object of the present invention to provide a method of extracting metal ions using the above novel bisquinolinol and bisbenzoquinolinol compounds.

In accomplishing the foregoing object, there is provided in accordance with the present invention a compound having the following general formula (I):

$$CH_2=C\diagup^{CH_2-R^1}_{\diagdown CH_2-R^1} \quad (I)$$

wherein $R^1$ represents a 8-hydroxy-7-quinolyl group which may have an alkyl group at the 2-position thereof or a 10-hydroxy-9-benzoquinolyl group which may have an alkyl group at the 2-position thereof.

In another aspect, the present invention provides a compound having the following general formula (II):

$$CH_2=C\diagup^{CH_2-O-R^2}_{\diagdown CH_2-O-R^2} \quad (II)$$

wherein $R^2$ represents a 8-quinolyl group which may have an alkyl group at the 2-position thereof or a 10-benzoquinolyl group which may have an alkyl group at the 2-position thereof.

The present invention also provides a process for the preparation of a compound having the following general formula (I):

$$CH_2=C\diagup^{CH_2-R^1}_{\diagdown CH_2-R^1} \quad (I)$$

wherein $R^1$ represents a 8-hydroxy-7-quinolyl group which may have an alkyl group at the 2-position thereof or a 10-hydroxy-9-benzoquinolyl group which may have an alkyl group at the 2-position thereof, said method comprising the steps of:

(a) reacting 2-chloromethyl-3-chloro-1-propene with a quinoline compound selected from 8-hydroxyquinoline which may have an alkyl group at the 2-position thereof and 10-hydroxyquinoline which may have an alkyl group at the 2-position thereof in the presence of a base to obtain an intermediate compound having the following general formula (II):

$$CH_2=C\diagup^{CH_2-O-R^2}_{\diagdown CH_2-O-R^2} \quad (II)$$

wherein $R^2$ represents a 8-quinolyl group which may have an alkyl group at the 2-position thereof or a 10-benzoquinolyl group which may have an alkyl group at the 2-position thereof; and (b) heating said intermediate compound of the formula (II) to obtain said compound of the formula (I).

The present invention further provides a method of extracting metal ions contained in an aqueous liquid, comprising contacting an extractant liquid containing a compound according to claim 1 dissolved in a water-insoluble organic solvent with said aqueous liquid so that the metal ions are captured by said compound and extracted by said extractant liquid.

Other objects, features and advantages of the present invention will become apparent from the detailed description of the preferred embodiments of the invention to follow.

DETAILED DESCRIPTION OF THE PREFERRED EMBODIMENTS OF THE INVENTION

The bisquinolinol and bisbenzoquinolinol derivatives according to the present invention having the above formula (I):

$$CH_2=C\diagup^{CH_2-R^1}_{\diagdown CH_2-R^1} \quad (I)$$

wherein $R^1$ represents a 8-hydroxy-7-quinolyl group which may have an alkyl group at the 2-position thereof or a 10-hydroxy-9-benzoquinolyl group which may have an alkyl group at the 2-position thereof, may be prepared by the following two step reactions:

First Step:

In the first step, 2-chloromethyl-3-chloro-1-propene is reacted with a quinoline compound selected from 8-hydroxyquinoline which may have an alkyl group at the 2-position thereof and 10-hydroxyquinoline which may have an alkyl group at the 2-position thereof in the presence of a base to obtain an intermediate, ether-containing, bisquinoline or bisbenzoquinoline compound having the following general formula (II):

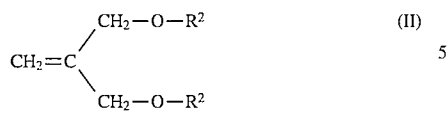

wherein $R^2$ represents a 8-quinolyl group which may have an alkyl group at the 2-position thereof or a 10-benzoquinolyl group which may have an alkyl group at the 2-position thereof.

The above reaction may be expressed as follows: when $R_2$ is 8-quinolyl group:

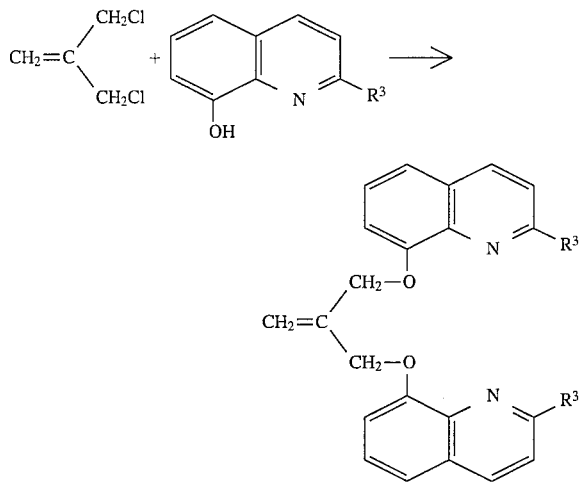

when $R_2$ is 10-benzoquinolyl group:

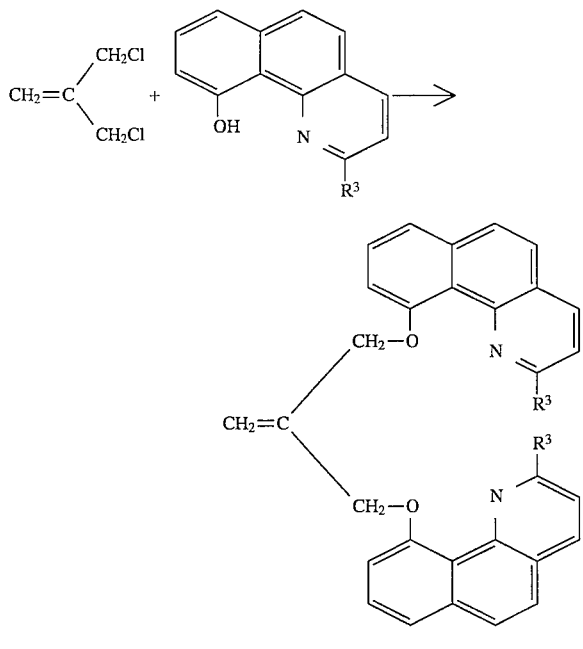

wherein $R^3$ represents an alkyl group, preferably a straight chain or a branched alkyl group having 1–12 carbon atoms, more preferably 1–4 carbon atoms.

The above reaction in the first step is performed at a temperature of 40°–150° C., preferably 70°–100° C. in the presence of a base. The quinoline compound is generally used in an amount of 2–3 moles, preferably 2–2.5 moles per mole of the 2-chloromethyl-3-chloro-1-propene. The base may be, for example, a metal alcoholate such as potassium tert-butoxide, sodium tert-butoxide or sodium ethoxide or a metal hydride such as sodium hydride. The base is generally used in an amount of 1–1.2 moles, preferably about 1 mole, per mole of the quinoline compound. An alkali metal iodide such as potassium iodide or sodium iodide may be used in conjunction with the base to accelerate the reaction. The reaction is suitably performed in the presence of a reaction solvent such as dimethylformamide or dimethylsulfoxide.

Second Step:

The thus obtained intermediate compound of the formula (II) is then heated to obtain the bisquinolinol or bisbenzoquinolinol compound of the formula (I). This reaction may be expressed as follows:

In the case of bisquinoline compound:

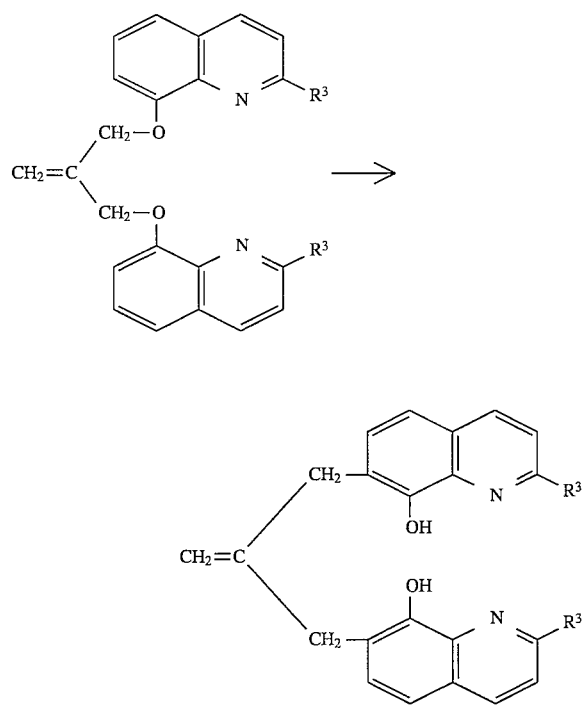

In the case of bisbenzoquinoline compound:

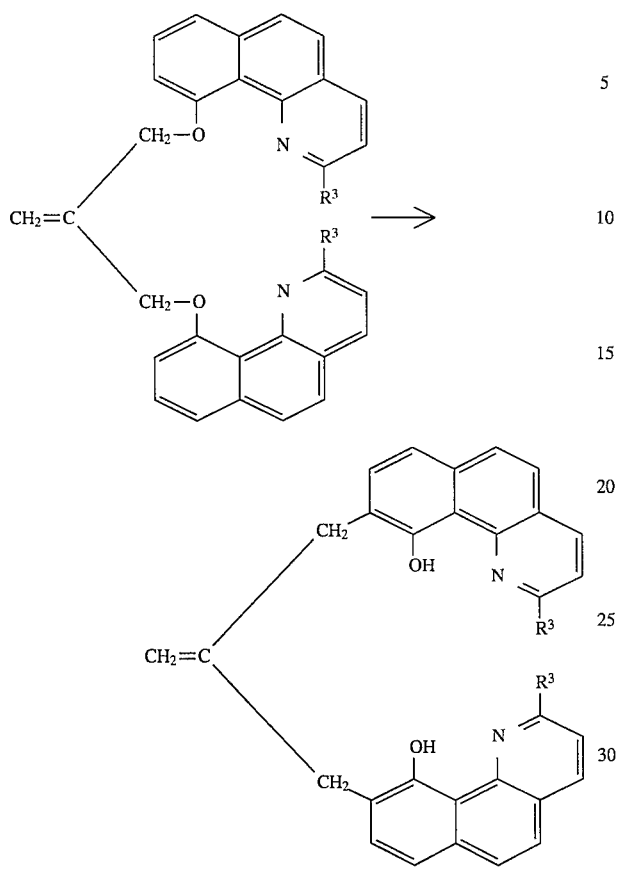

The above rearrangement is generally performed at a temperature of 170°–250° C., preferably 180°–200° C., in the absence of a solvent.

The bisquinoline and bisbenzoquinoline compounds of the formula (I) can capture metal ions such as copper ions, nickel ions, cobalt ions, zinc ions, palladium ion, cadmium ions and mercury ions, especially divalent metal ions, and, therefore, can be used for selectively extracting such metal ions.

The extraction of metal ions can be done by contacting a first, metal ion-containing liquid, generally an aqueous liquid having a pH of about 1–7 with a second liquid, generally an organic solvent solution, containing the compound of the formula (I) and substantially immiscible with the first liquid so that the metal ions may be captured by the compound of the formula (I). Illustrative of suitable organic solvents are halogenated organic solvents such as chloroform, carbon tetrachloride and dichloroethane; hydrocarbons such as benzene, toluene and xylene; and alcohols such as hexanol and octanol. The concentration of the compound of the formula (I) in the second liquid is generally in the range of $1\times10^{-6}$ to 1 mol/liter, preferably $1\times10^{-5}$ to $1\times10^{-1}$ mol/liter.

The following examples will further illustrate the present invention.

EXAMPLE 1

Synthesis of 2-(8-hydroxy-7-quinolyl)methyl-3-(8-hydroxy-7-quinolyl)-1-propene (Compound 1):

Into 50 ml of dimethylformamide were dissolved 7.0 g (0.048 mol) of 8-quinolinol, to which 5.0 g (0.045 mol) of potassium tert-butoxide were added. The resulting mixture was stirred until a gas ceased generating and the liquid became transparent and thereafter mixed with 2.5 g (0.020 mol) of 2-chloromethyl-3-chloro-1-propene and a small amount of potassium iodide. The mixture was reacted at 70° C. for 24 hours with stirring. The reaction mixture was then cooled to room temperature, mixed with 150 ml of water and extracted thrice with 50 ml of benzene. The benzene phase was washed thrice with 100 ml of water and dried over anhydrous magnesium sulfate. The benzene was removed in vacuo and the residue was subjected to silica gel chromatography using chloroform as an elution liquid, thereby to separate 1.6 g (yield: 47%) of 2-(8-quinolyloxy)methyl-3-(8-quinolyloxy)-1-propene as a colorless solid having a melting point of about 101°–102° C. The chemical structure of this intermediate product was elucidated by NMR, IR and MS. The mass spectrometric analysis gave a molecular weight of 342.1375 (calculated: 342.1367 as $C_{22}H_{18}N_2O_2$).

The intermediate product (0.6 g) was heated at 200° C. for 2 hours without using any solvent. After cooling, the heat-treated product was subjected to silica gel chromatography using chloroform as an elution liquid, thereby separating 0.54 g (yield: 90%) of Compound 1 as a colorless solid having a melting point of about 131°–132° C. The chemical structure of this product was elucidated by NMR, IR and MS. The mass spectrometric analysis gave a molecular weight of 342.1331 (calculated: 342.1367 as $C_{22}H_{18}N_2O_2$).

EXAMPLE 2

Synthesis of 2-(8-hydroxy-7-quinolyl)methyl-3-(2-methyl-8-hydroxy-7-quinolyl)-1-propene (Compound 2):

Example 1 was repeated in the same manner as described except that 7.0 g (0.044 mol) of 2-methyl-8-quinolinol were substituted for the 7.0 g of 8-quinolinol, thereby obtaining 3.8 g (yield: 51%) of 2-(2-methyl-8-quinolyloxy)methyl-3-(2-methyl-8-quinolyloxy)-1-propene as a colorless solid having a melting point of about 77°–79° C. The chemical structure of this intermediate product was elucidated by NMR, IR and MS. The mass spectrometric analysis gave a molecular weight of 370.1685 (calculated: 370.1680 as $C_{24}H_{22}N_2O_2$).

The intermediate product (0.96 g) was heated at 200° C. for 2 hours without using any solvent. After cooling, the heat-treated product was subjected to silica gel chromatography using chloroform as an elution liquid, thereby separate 0.84 g (yield: 88%) of Compound 2 as a light yellow solid having a melting point of about 177°–178° C. The chemical structure of this product was elucidated by NMR, IR and MS. The mass spectrometric analysis gave a molecular weight of 370.1657 (calculated: 370.1680 as $C_{24}H_{22}N_2O_2$).

EXAMPLE 3

Synthesis of 2-(10-hydroxy-9-benzoquinolyl)methyl-3-(10-hydroxy-9-benzoquinolyl)-1-propene (Compound 3):

Example 1 was repeated in the same manner as described except that 2.1 g (0.011 mol) of 10-benzoquinolinol were substituted for the 7.0 g of 8-quinolinol, thereby obtaining 0.7 g (yield: 32%) of 2-(10-benzoquinolyloxy)-methyl-3-(10-quinolyloxy)-1-propene as a light yellow solid having a melting point of about 112°–114° C. The chemical structure of this intermediate product was elucidated by NMR, IR and MS. The mass spectrometric analysis gave a molecular weight of 442.1658 (calculated: 442.1680 as $C_{30}H_{22}N_2O_2$).

The intermediate product (0.15 g) was heated at 200° C. for 2 hours without using any solvent. After cooling, the heat-treated product was subjected to silica gel chromatography using chloroform as an elution liquid, thereby separate 1.3 g (yield: 87%) of Compound 3 as a yellow solid having a melting point of about 141°–144° C. The chemical structure of this product was elucidated by NMR, IR and MS. The mass spectrometric analysis gave a molecular weight of 442.1691 (calculated: 442.1680 as $C_{30}H_{22}N_2O_2$).

Extraction Performance of Compounds 1–3:

EXAMPLE 4

A first, aqueous solution (5 ml) having a pH of 6.2 and containing 0.1 mM of $Cu(OCOCH_3)_2$ and a second solution (5 ml) containing Compound 1 dissolved in chloroform were placed in a 20 ml tube and the tube was shaken at 25° C. for 2 hours. The organic layer was separated and measured for the extraction yield by the atomic absorption analysis. The extraction yield is calculated according to the following equation:

Extraction Yield (%)=$C_1/C_0 \times 100$ wherein $C_1$ represents the amount of the metal ion in the first solution and $C_0$ represents the amount of the metal ion in the organic layer. The results are shown in Table 1.

The above procedure was repeated in the same manner as described except that $Cu(OCOCH_3)_2$ was substituted with $Ni(OCOCH_3)_2$, $Co(OCOCH_3)_2$ or $Zn(OCOCH_3)_2$. The results are summarized in Table 1.

TABLE 1

Extraction performance of Compound 1 for aqueous solution containing single kind of metal ions

| Metal Ion | Extraction Yield (%) |
|---|---|
| $Cu^{++}$ | 100 |
| $Ni^{++}$ | 95 |
| $Co^{++}$ | 100 |
| $Zn^{++}$ | 100 |

EXAMPLE 5

A first, aqueous solution (5 ml) having a pH of 6.2 and containing 0.1 mM of $CU(OCOCH_3)_2$, 0.1 mM of $Ni(OCOCH_3)_2$, 0.1 mM of $Co(OCOCH_3)_2$ and 0.1 mM of $Zn(OCOCH_3)_2$ and a second solution (5 ml) containing Compound 1 dissolved in chloroform were placed in a 20 ml tube and the tube was shaken at 25° C. for 2 hours. The organic layer was separated and measured for the extraction yield by the atomic absorption analysis. The results are summarized in Table 2.

TABLE 2

Extraction performance of Compound 1 for aqueous solution containing four kinds of metal ions

| Metal Ion | Extraction Yield (%) |
|---|---|
| $Cu^{++}$ | 100 |
| $Ni^{++}$ | 67 |
| $Co^{++}$ | 100 |
| $Zn^{++}$ | 97 |

EXAMPLE 6

Example 4 was repeated in the same manner as described except that Compound 2 was substituted for Compound 1. The results are summarized in Table 3.

TABLE 3

Extraction performance of Compound 2 for aqueous solution containing single kind of metal ions

| Metal Ion | Extraction Yield (%) |
|---|---|
| $Cu^{++}$ | 100 |
| $Ni^{++}$ | 42 |
| $Co^{++}$ | 4 |
| $Zn^{++}$ | 90 |

EXAMPLE 7

Example 5 was repeated in the same manner as described except that Compound 2 was substituted for Compound 1. The results are summarized in Table 4.

TABLE 4

Extraction performance of Compound 2 for aqueous solution containing four kinds of metal ions

| Metal Ion | Extraction Yield (%) |
|---|---|
| $Cu^{++}$ | 100 |
| $Ni^{++}$ | 17 |
| $Co^{++}$ | 0 |
| $Zn^{++}$ | 76 |

EXAMPLE 8

Example 4 was repeated in the same manner as described except that Compound 3 was substituted for Compound 1. The results are summarized in Table 5.

TABLE 5

Extraction performance of Compound 3 for aqueous solution containing single kind of metal ions

| Metal Ion | Extraction Yield (%) |
|---|---|
| $Cu^{++}$ | 64 |
| $Ni^{++}$ | 5 |
| $Co^{++}$ | 0 |
| $Zn^{++}$ | 0 |

EXAMPLE 9

Example 5 was repeated in the same manner as described except that Compound 3 was substituted for Compound 1. The results are summarized in Table 6.

TABLE 6

Extraction performance of Compound 3 for aqueous solution containing four kinds of metal ions

| Metal Ion | Extraction Yield (%) |
|---|---|
| $Cu^{++}$ | 68 |
| $Ni^{++}$ | 0 |
| $Co^{++}$ | 0 |
| $Zn^{++}$ | 0 |

EXAMPLE 10

Example 4 concerning the extraction of cupric ions was repeated in the same manner as described except that the pH of the cupric ion-containing aqueous solution was varied as shown in Table 7. The results are also shown in Table 7.

COMPARATIVE EXAMPLE 1

Example 10 was repeated in the same manner as described except that a chloroform solution containing 2 mM of 5-octyloxymethyl-8-quinolinol was used in lieu of the second solution containing 1 mM of Compound 1. The results are summarized in Table 7.

TABLE 7

Extraction performance of Compound 1 and comparative extractant for cupric ion solutions having various pH

| Extractant Concentration | Extraction Yield (%) | |
|---|---|---|
| | Compound 1 1 mM | Comparative 2 mM |
| pH: 6.2 | 100 | 100 |
| 5.9 | 100 | 100 |
| 5.2 | 100 | 100 |
| 4.3 | 100 | 100 |
| 3.8 | 100 | 100 |
| 3.2 | 100 | 100 |
| 2.6 | 100 | 98 |
| 1.4 | 44 | 15 |

The results shown in Table 7 indicate that Compound 1 has higher extracting power and lower pH dependency as compared with the comparative extractant.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

What is claimed is:

1. A compound having the following general formula (I):

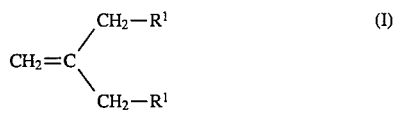 (I)

wherein said $R^1$ groups are the same and $R^1$ is selected from the group consisting of

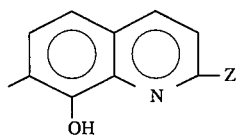

where Z is H or alkyl
and

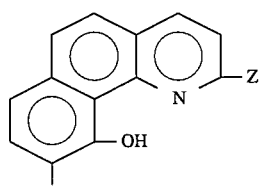

where Z is H or alkyl.

2. A compound having the following general formula (II):

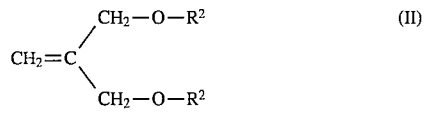 (II)

wherein said $R^2$ groups are the same and R2 is selected from the group consisting of

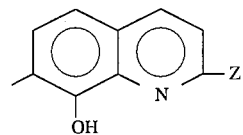

where Z is H or alkyl
and

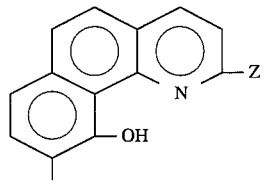

where Z is H or alkyl.

3. A process for the preparation of a compound having the following general formula (I):

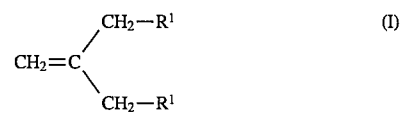 (I)

wherein said $R^1$ groups are the same and $R^1$ is selected from the group consisting of

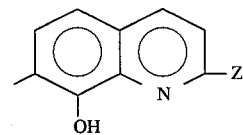

where Z is H or alkyl
and

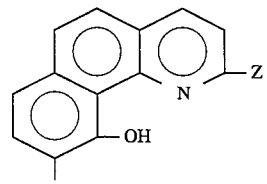

where Z is H or alkyl (a) reacting 2-chloromethyl-3-chloro-1-propene with a quinoline compound selected from the group consisting of 8-hydroxyquinoline which may have an alkyl group at the 2-position thereof and 10-hydroxyquinoline which may have an alkyl group at the 2-position thereof in the presence of a base to obtain an intermediate compound having the following general formula (II):

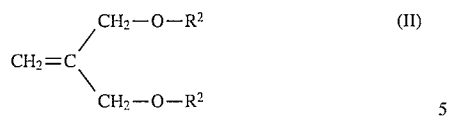

(II)

wherein R² represents a 8-quinolyl group which may have an alkyl group at the 2-position thereof or a 10-benzoquinolyl group which may have an alkyl group at the 2-position thereof; and (b) heating said intermediate compound to obtain said compound of the formula (II).

4. A method of extracting divalent metal ions from an aqueous liquid having a pH of 1–7 and containing the metal ions, comprising:

contacting said aqueous liquid with an extractant liquid containing, dissolved in a water-insoluble organic solvent, $10^{-6}$ to 1 mol/liter of a compound having the following general formula (I):

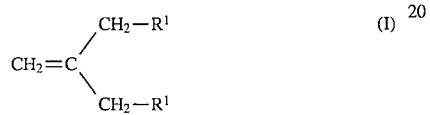

(I)

wherein said R¹ groups are the same and R¹ is selected from the group consisting of:

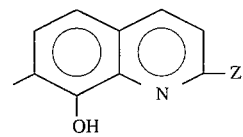

where Z is H or alkyl and

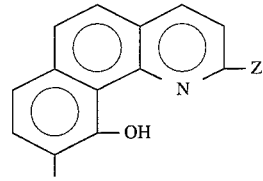

where Z is H or alkyl whereby the metal ions are captured by said compound and extracted by said extractant liquid from said aqueous liquid.

\* \* \* \* \*

UNITED STATES PATENT AND TRADEMARK OFFICE
CERTIFICATE OF CORRECTION

PATENT NO. : 5,599,935
DATED : February 4, 1997
INVENTOR(S) : HIRATANI et al

It is certified that error appears in the above-identified patent and that said Letters Patent is hereby corrected as shown below:

The formula at col. 5, lines 10-15 reads:

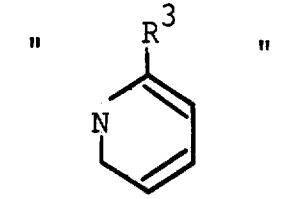

should read:

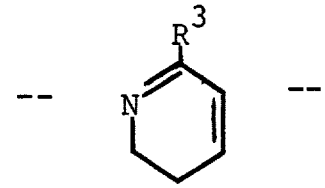

The formula at col. 3, lines 51-57 reads

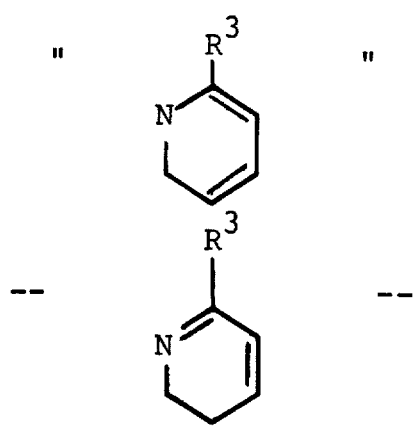

should read:

Signed and Sealed this

Ninth Day of December, 1997

Attest:

*Bruce Lehman*

BRUCE LEHMAN

*Attesting Officer*    *Commissioner of Patents and Trademarks*